(12) United States Patent
Kunin

(10) Patent No.: US 8,784,852 B2
(45) Date of Patent: Jul. 22, 2014

(54) TOPICAL SKIN CARE COMPOSITION

(76) Inventor: Audrey Kunin, Mission Hills, KS (US)

(*) Notice: Subject to any disclaimer, the term of this patent is extended or adjusted under 35 U.S.C. 154(b) by 437 days.

(21) Appl. No.: 12/395,251

(22) Filed: Feb. 27, 2009

(65) Prior Publication Data

US 2010/0221245 A1 Sep. 2, 2010

(51) Int. Cl.
*A61K 8/02* (2006.01)
*A61K 31/075* (2006.01)

(52) U.S. Cl.
USPC .......................................... 424/401; 514/714

(58) Field of Classification Search
None
See application file for complete search history.

(56) References Cited

U.S. PATENT DOCUMENTS

| | | | |
|---|---|---|---|
| 7,169,401 B2 * | 1/2007 | Puglia et al. | 424/401 |
| 7,326,420 B2 * | 2/2008 | Burkhart et al. | 424/400 |
| 2004/0018241 A1 * | 1/2004 | Houze et al. | 424/486 |
| 2004/0228885 A1 * | 11/2004 | Khaiat et al. | 424/401 |
| 2005/0048008 A1 * | 3/2005 | Gupta | 424/59 |
| 2006/0135822 A1 * | 6/2006 | Schwarz et al. | 568/559 |
| 2008/0119527 A1 * | 5/2008 | Baldo | 514/355 |

OTHER PUBLICATIONS

Russell, Topical Therapy for Acne, American Family Physician, Jan. 15, 2000.*
Ahmad N, Muktar H, Cutaneous photochemoprotection by green tea: a brief review., Abstract from Skin Pharmacol Appl Skin Physiol, Mar.-Apr. 2001, pp. 69-76, Volume-Issue 14(2).
Gonzales M, Bowden GT, Nordihydroguaiaretic acid-mediated inhibition of ultraviolet B-induced activator protein-1 activation in human keratinocytes, Abstract from Mol Carcinog, 2002, pp. 102-111, Volume-Issue 34(2).
Liu J., Pharmacology of oleanolic acid and ursolic acid., Abstract from J Ethnopharmacol, Dec. 1, 1995, pp. 57-68, Volume-Issue 49(2).
James J. Leyden, M.D., Therapy for Acne Vulgaris, The New England Journal of Medicine, Apr. 17, 1997, pp. 1156-1162, Volume-Issue 336, No. 16.
M Mikuni, M Yoshida, P Hellberg, CA Peterson, SS Edwin, M Brannstrom, CM Peterson, The lipoxygenase inhibitor, nordihydroguaiaretic acid, inhibits ovulation and reduces leukotriene and prostaglandin levels in the rat ovary, Biology of Reproduction, 1998, pp. 1211-1216, vol. 58.
Matthias Schöttner, Gerhard Spiteller, Lignans Interfering with 5α-Dihydrotestosterone Binding to Human Sex Hormone-Binding Globulin, J. Nat. Prod., 1998, pp. 119-121, vol. 61.
Hisashi Matsuda, Yuhao Li, Toshiyuki Murakami, Johji Yamahara, Masayuki Yoshikawa, Protective effects of oleanolic acid oliglycosides on ethanol- or indomethacin-induced gastric mucosal lesions in rats, Abstract from Life Sciences, Sep. 18, 1998, pp. PL245-PL250, Volume-Issue 63, 17.
John J. Russell, M.D., Topical Therapy for Acne, American Family Physician, Jan. 15, 2000.

Katiyar SK, Ahmad N, Mukhtar H, Green Tea and Skin, Abstract from Arch Dermatol, 2000 Aug, pp. 989-994, Volume-Issue 136(8).
Hiipakka RA, Zhang HZ, Dai W, Dai Q, Liao S., Structure-activity relationships for inhibition of human 5alphareductases by polyphenols., Abstract from Biochem Pharmacol., Mar. 15, 2002, pp. 1165-1176, Volume-Issue 63(6).
Wenchieh Chen, Diane Thiboutot, Christos C Zouboulis, Cutaneous Androgen Metabolism: Basic Research and Clinical Perspectives, Abstract from Journal of Investigative Dermatology, 2002, pp. 992-1007, vol. 119.
Daniel B. Yarosh, Jason W. Galvin, Stephanie L. Nay, Arely V. Peña, Matthew T. Canning, David A. Brown, Anti-inflammatory activity in skin by biomimetic of *Evodia rutaecarpa* extract from traditional Chinese medicine, Journal of Dermatological Science, 2006, pp. 13-21, vol. 42.
Gustavo Moura-Letts, León F. Villegas, Ana Marçalo, Abraham J Vaisberg, Gerald B. Hammond, In Vivo Wound-Healing Activity of Oleanolic Acid Derived from the Acid Hydrolysis of *Anredera diffusa*, Abstract from J. Nat. Prod., 2006, pp. 978-979, Volume-Issue 69(6).
Mei-Chin Yin, Kung-Chi-Chan, Nonenzymatic Antioxidative and Antiglycative Effects of Oleanolic Acid and Ursolic Acid, Abstract from J. Agric. Food Chem., Jul. 21, 2007.
Iwata H, Tezuka Y, Kadota S, Hiratsuka A, Watabe T, Mechanism-based inactivation of human liver microsomal CYP3A4 by rutaecarpine and limonin from Evodia fruit extract., Abstract from Drug Metab Pharmacokinet., 2005, pp. 34-45, Issue-vol. 20(1).
GeroNova Research, Inc., NDGA: Norhidydroguaiaretic Acid, 2005.
C.A. Kontogiorgis, D.J. Hadjipavlou-Littina, Non Steroidal Anti-Inflammatory and Anti-Allergy Agents.
American Cancer Society, Inc., Making Treatment Decisions, 2008. http://www.pdrhealth.com, Quercetin.
Singh S, Khajuria A, Taneja SC, Johri RK, Singh J, Qazi GN, Boswellic acids: A leukotriene inhibitor also effective through topical application in inflammatory disorders. Abstract from Phytomedicine, Epub. Jan. 26, 2008.
Memorial Sloan-Kettering Cancer Center, About Herbs - Boswellia (Boswellia Serrata), 2006.
Bermejo Benito P, Abad Martinez MJ, Silvan Sen AM, Sanz Gomez A, Fernandez Matellano L, Sanchez Contreras S, Diaz Lanza AM, In vivo and in vitro antiinflammatory activitiy of saikosaponins., Abstract from Life Sci., 1998, pp. 1147-1156, Volume-Issue 63(13).
Ho YL, Chang YS, Studies on the antinociceptive, anti-inflammatory and anti pyretic effects of Isatis indigotica root., Abstract from Phytomedicine, Jul. 2002, pp. 419-24, Volume-Issue 9(5).
Memorial Sloan-Kettering Cancer Center, About Herbs—Isatis Root (Radix isatidis baphicacanthi, *Isatis tinctoria, Isatis indigotica*), 2006.
Jones LH, Abdalla DS, Freitas JC, Effects of indole-3-acetic acid on croton oil- and arachidonic acid-induced mouse ear edema., Abstract from Inflamm Res., 1995, pp. 372-5, Volume-Issue 44(9).
Salugenecists, Inc., Botanical: *Boswellia* sp., 2001-2005.

(Continued)

*Primary Examiner* — David J Blanchard
*Assistant Examiner* — Tigabu Kassa
(74) *Attorney, Agent, or Firm* — Husch Blackwell LLP

(57) ABSTRACT

The present invention is directed to a topical skin care composition. The composition has the unique ability to treat acne without drying out the user's skin. In particular, the composition includes a base, an antibacterial agent, at least one anti-inflammatory agent, and at least one antioxidant. The antibacterial agent may be benzoyl peroxide.

1 Claim, No Drawings

(56) References Cited

OTHER PUBLICATIONS

Ammon HP, Safayhi H, Mack T, Sabieraj J, Mechanism of anti-inflammatory actions of curcumine and boswellic acids, Abstract from J Ethnopharmacol, Mar. 1993, pp. 113-9, Issue-vol. 38(2-3).

Asia Pacific Personal Care, Natural Extract Has Healing Properties, Nov. 2005.

Smart Nutrition, Serrapeptase: Silkworm Enzyme.

MedlinePlus, Polypodium leucotomos extract and anapsos, Sep. 1, 2005.

Dreher F, Maibach H, Protective Effects of Topical Antioxidants in Humans, Abstract from Curr Probl Dermatol., 2001, pp. 157-164, vol. 29.

Nusgens BV, Humbert P, Rougier A, et al, Topically Applied Vitamin C Enhances the mRNA Level of Collagens I and III, Their Processing Enzymes and Tissue Inhibitor of Matrix Metalloproteinase 1 in the Human Dermis, Abstract from J Invest Dermato., 2001, pp. 853-849, vol. 116.

Katiyar SK, Elmets CA, Green Tea Polyphenolic Antioxidants and Skin Photoprotection, Abstract from Int J Oncol., 2001, pp. 1307-13013, vol. 18.

Katiyar SK, Mukhtar H, Green Tea Polyphenol (-)-Epigallocatechin-3-gallate Treatment to Mouse Skin Prevents UVB-Induced Infiltration of Leukocytes, Depletion of Antigen-Presenting Cells, and Oxidative Stress, Abstract from J. Leukoc Biol., 2001, pp. 719-726, vol. 69.

Moison RM, Steenvoorden DP, Beijersbergen Van Henegouwen GM, Topically Applied Eicosapentaenoic Acid Protects Against Local Immunosuppression Induced by UVB Irradiation, Cis-urocanic acid and Thymidine Dinucleotides, Abstract from Photochem Photobiol., 2001, pp. 64-70, vol. 73.

Thiele JJ, Schroeter C, Hsieh SN, Podda M, Packer L, The Antioxidant Network of the Stratum Corneum, Abstract from Curr Probl Dermatol., 2001, pp. 26-42, vol. 29.

Thang PT, Patrick S, Teik LS, Yung CS, Anti-Oxidant Effects of the Extracts From the Leaves of *Chromolaena odorata* on Human Dermal Fibroblasts and Epidermal Keratinocytes Against Hydrogen Peroxide and Hypoxanthine-Xanthine Oxidase Indicate Damage, Abstract from Burns, 2001, p. 319-327, vol. 27.

Thiele JJ, Oxidative Targets in the Stratum Corneum. A New Basis for Antioxidative Strategies, Abstract from Skin Pharmacol Appl Skin Physiol., 2001, pp. 87-91, vol. 14.

Nyska A, Lomnitski L, Spalding J, et al, Topical and Oral Administration of the Natural Water-Soluble Antioxidant From Spinach Reduces the Multiplicity of Papillomas in the Tg.AC Mouse Model, Abstract from Toxicol Lett, 2001, pp. 33-44, vol. 122.

Pinnell SR, Yang H, Omar M, et al, Topical I-ascorbic Acid: Percutaneous Absorption Studies, Abstract from Dermatol Surg., 2001, pp. 137-142, vol. 27.

\* cited by examiner

TOPICAL SKIN CARE COMPOSITION

BACKGROUND OF THE INVENTION

The present invention generally relates to compositions and methods for producing topical skin care. Acne vulgaris, or acne, is a common skin disease that is prevalent in teenagers and young adults. Acne is associated with low self-esteem and social inhibition in those that suffer from acne especially if it is particularly severe. Several factors may contribute to the development of acne. The primary problem being the abnormal flaking of cells inside the hair follicle that leads to the formation of a plug. The plug can enlarge and even rupture the hair follicle. A ruptured hair follicle spills its contents of oil and debris into the skin where it leads to swelling and causes redness (inflammation). Naturally-occurring bacteria known as *Propionibacterium acnes* may also be responsible for causing acne. These bacteria produce substances that cause redness and irritation (inflammation) and also make enzymes that dissolve the sebum (oil from oil glands in the skin) and thereby create irritating substances that can make the inflammation worse.

Certain hormones called androgens can be an additional factor in causing acne. Androgens are male hormones that are present in both men and women and both enlarge the sebaceous glands in the skin as well as cause glands to increase sebum production. The increased sebum leads to plug formation and serves as more "food" for the bacteria. Androgens surge at puberty which contributes to the development of acne in teenagers and young adults.

Hair follicles exist on virtually all skin except for the palms of the hands and soles of the feet. Inside the follicle, the hair extends up from the deep layers of the skin and comes out of a pore. Near the surface, the oil gland (sebaceous gland) enters the hair follicle where it empties sebum at a relatively constant rate. The sebum lubricates the skin and provides a protective barrier to prevent drying. Skin on the face, chest, and back has an especially large number of sebaceous glands. These are the areas where acne is most likely to occur.

There are two major types of acne lesions: noninflammatory and inflammatory. Noninflammatory acne lesions include blackheads (open comedones) and whiteheads (closed comedones). Open and closed comedones along with papules and pustules are commonly referred to as papulopustular acne which is a form of inflammatory acne. Nodular acne is the most severe form of inflammatory acne. Open comedones result from the enlargement and dilation of a plug that forms from oil and flakes of skin inside the hair follicle. A closed comedone forms if the hair follicle pore remains closed. Inflammatory acne lesions consist of red blemishes, pimples (papules, pustules), and larger, deeper, swollen, and tender lesions (nodules). Papules are closed comedones that have become red, swollen, and inflamed. Pustules are closed comedones that become inflamed and begin to rupture into the skin forming pustular heads of various sizes. Nodules represent large, tender, swollen acne lesions that have become intensely inflamed and rupture under the skin. If left untreated, these nodules can produce deep scarring.

There are a variety of topical therapies available to treat and prevent acne. Topical retinoids such as tretinoin or adapalene are effective for treating comedonal acne. Inflammatory lesions benefit from treatment with benzoyl peroxide, azelaic acid or topical antibiotics. Benzoyl peroxide, in over-the-counter and prescription formulations, has been a mainstay of acne treatment since the 1950s. Skin irritation is the most common side effect of benzoyl peroxide and other antibiotic usage. Some treatments can be severe and can leave the user's skin excessively dry. Excessive use of some acne products may cause redness, dryness of the face, and can actually lead to more acne. Therefore, it would be beneficial to provide an effective acne treatment that also calms the user's skin and does not have a drying effect.

Even good acne treatments may not be able to prevent all breakouts of acne. Treatments, such as masks, that are developed specifically to target an acne breakout or appearance of a blemish tend to leave the skin drier and are not always effective. Therefore, it would be beneficial to provide an acne treatment that could target a specific breakout or blemish that does not have a drying effect on the user's skin.

Another known treatment of acne and acne breakouts is cortisone injection therapy. Cortisone injection therapy may be very useful as a method of treating acne; however these shots can be painful and do not get at the root cause of the acne. Cortisone injection therapy is also not suggested for long-term treatment. Therefore, it would be beneficial to provide a topical acne treatment that could specifically target a breakout or blemish but could also be used for long-term treatment of acne.

SUMMARY OF THE INVENTION

The present invention generally relates to topical skin care compositions and methods for treatment of acne. The skin care composition hereof has the unique ability to treat acne without drying out the user's skin. In particular, a topical skin care composition is provided that includes a base, an antibacterial agent, at least one anti-inflammatory agent and at least one antioxidant. In one non-limiting illustration, the composition contains benzoyl peroxide, evodia rutaecarpa, boswellia serrata, quercetin, oleanolic acid, and tea extracts.

DETAILED DESCRIPTION OF THE INVENTION

There is provided herein a topical skin care composition that treats acne without drying out the user's skin. The skin care composition hereof generally includes a base, an antibacterial agent, at least one anti-inflammatory agent, and at least one antioxidant. It will be appreciated by those skilled in the art that some agents disclosed throughout may have two or more properties; for example, benzoyl peroxide can act as both an antibacterial agent as well as an anti-inflammatory agent.

In one embodiment, the skin care composition includes an effective amount of a base. In certain embodiments, the base is present in an amount of from about 1.0 to 100.0 w/w % of the composition, more preferably from about 10.0 to 95.0 w/w %, and most preferably from about 20 to 95 w/w %. Preferred bases include, but are not limited to, soaps, washes, lotions, creams, gels, masks, ointments, solutions, scrubs, microdermabrasion creams, serums, strips, patches, and combinations thereof.

In one embodiment, the skin care composition may also include an effective amount of an antibacterial agent. In certain embodiments, the antibacterial agent is present in an amount of from about 0.001 to 20.0 w/w % of the composition, more preferably from about 0.15 to 10.0 w/w %, and most preferably about 5 w/w %. In certain other embodiments, the antibacterial agent is benzoyl peroxide and is preferably about 5 w/w % of the skin care composition.

In addition to benzoyl peroxide, other antibacterial agents suitable for use in the present invention include, but are not limited to, bacitracin, polymyxin B, neomycin, mupirocin, hydrastine, aminopropanesulphonic acid, acetohydroxamic acid, actinonin, actinospectacin, aklavin hydrochloride, alexidine hydrochloride, amikacin sulfate, amoxicillin, ampicillin sodium, azithromycin, azlocillin sodium, bacampicillin hydrochloride, bacitracin, becanamycin, butirosin A, camphor, cannabidiol, capreomycin sulfate, carbenicillin disodium, cefadroxil, cefazolin sodium, cefotaxime sodium, cephalosporin sodium, cephalothin sodium, cephapirin sodium, cephradine sodium, chloramphenicol hemisuccinate, chloramphenicol, chlorhexidine, chloroxylenol, chlortetracycline, ciprofloxacin, clindamycin hydrochloride, clofoctol, cloxacillin sodium, cloxyquin, colistimethate sodium, cycloserine, dapsone, demeclocycline hydrochloride, dibekacin, dihydrostreptomycin sulfate, doxycycline hydrochloride, enoxacin, erythromycin estolate, erythromycin ethylsuccinate, erythromycin propionate lauryl sulfate, erythromycin stearate, erythromycin, ethambutol dihydrochloride, ethionamide, flumequine, fusidic acid, gambogic acid, gentamicin sulfate, gentian violet, haloprogin, helenine, hetacillin potassium, isoniazid, kanamycin sulfate, kojic acid, lividomycin A, mafenide hydrochloride, meclocycline sulfosalicylate, methacycline hydrochloride, methicillin sodium, minocycline hydrochloride, moxalactam disodium, nafcillin sodium, neomycin sulfate, nigericin sodium, nitrofurantoin, norfloxacin, novobiocin sodium, oleandomycin phosphate, oligomycin, oxacillin sodium, oxytetracycline, parachlorophenol, paromomycin sulfate, patulin, penicillin G potassium, penicillin V potassium, phenethicillin potassium, piperacillin sodium, piperine, polymyxin B sulfate, pyrithione zinc, roxarsone, sisomicin sulfate, streptomycin sulfate, sulfabenzamide, sulfacetamide, sulfachlorpyridazine, sulfadiazine, sulfadimethoxine, sulfaguanidine, sulfameter, sulfamerazine, sulfamethazine, sulfamethizole, sulfamethoxazole, sulfamethoxypyridazine, sulfamonomethoxine, sulfanilamide, sulfanitran, sulfaphenazole, sulfaquinoxaline sodium, sulfathiazole, sulfisoxazole, thiamphenicol, trimethoprim, vancomycin hydrochloride, vulpinic acid, tyrothricin, derivatives thereof, or mixtures thereof In one embodiment of the present invention, the skin care composition also includes an effective amount of an antiinflammatory agent. In certain embodiments, the antiinflammatory agent is present in an amount of from about 1.0 to 20.0 w/w % of the composition, more preferably from about 5.0 to 15.0 w/w %, and most preferably from about 10.0 to 15.0 w/w %. Suitable anti-inflammatory agents include, but are not limited to, evodia rutaecarpa extract, boswellia serrata extract, quercetin, derivatives thereof, or mixtures thereof. Evodia rutaecarpa extract, also known as Wu-Zhu-Yu, has anti-inflammatory properties when applied topically to human skin. Boswellia serrata is a medium- to large-sized branching tree found in dry hilly areas of India, North Africa, and the Middle East. The boswellia tree exudates terpenoids, oils and gum resins that are collectively called baswellic acids and have an anti-inflammatory action much like conventional nonsteroidal agents. Boswellia inhibits pro-inflammatory mediators in the body, specifically leukotrienes via inhibition of 5-lipoxygenase. However, in contrast to conventional nonsteroidal anti-inflammatorv drugs, boswellia significantly reduces glycosaminoglycan degradation and therefore long-term use of boswellia does not lead to irritation and has a soothing effect on human skin. Quercetin is a flavonoid and has antioxidant and anti-inflammnatory activities.

Other suitable anti-inflammatory agents for use in the present invention include, but are not limited to, benzoyl peroxide, benzoyl peroxide and clindamycin combinations, clindamycin, erythromycin, tetracycline, alpha hydroxyl acid, salicylic acid, filipendula and meadowsweet, curled dock (rumex crispus), licorice extract, acetaminophen, acetylsalicyclic acid, acetic acid, zinc oxide, zinc sulfate, hydrocortisone, prednisone, solumedrol, prednisolone, white tea extract, green tea extract, caffeine, tannis, isatsis indigotica root extract, menthol, 18alpha-glcyrrhetinic acid, naproxen, 3-methyl-1-phenyl-2-pyrazolin-5-one, acacetin, acemetacin, aesculin, amcinonide, amiprilose, amygdalin, budesonide, bufexamac, gynnestemma, enoxolone, esculin, etodolac, fenbufen, fenoprofen, flufenamic acid, flumethasone, flumethazone pivalate, flunisolide, fluocinolone acetonide, fluocinonide, fluorometholone, flurandrenolide, flurbiprofen, fosfosal, gentisic acid, guaiazulene, halcinonide, hecogenin, hydrocortisone butyrate, ibuprofen, indomethacin, idnoprofen, isoxicam, ketoprofen, ketorolac tromethamine, mefenamic acid, n-(9-fluorenylmethoxycarbonyl)-1-leucine, nabumetone, nifenazone, niflumic acid, nimesulide, nordihydroguaretic acid, DHT inhibitors, nordihydroguaiaretic acid, spironolactone, drosperinone, propecia, BCPS, parthenolide, oxypenbutazone, picrolimus, ramiphenazone, sodium dichlofenac, sodium meclofenamate, solasodine, sulindac, suprofen, suxibuzone, tacrolimus, tenoxicam, tolfenamic acid, tripelennamine citrate, triprolidine hydrochloride, zomepirac sodium, aspirin, beclomethasone dipropionate, carbenoxolone sodium, celastrol, clobetasol propionate, dexamethasone acetate, dexmethasone sodium phosphate, diclofenac, diflucortolone pivalate, diflunisal, fenspiride hydrochloride, hydrocortisone acetate, hydrocortisone hemisuccinate, phenylbutazone, piroxicam, pregnenolone, triamcinolone acetonide, triamcinolone benetonide, triamcinolone diacetate, flutamide, cyproterone acetate, finasteride, aminolevulinic acid HCL, derivatives thereof, and mixtures thereof.

In addition, other suitable anti-inflammatory agents for use in the present invention include, but are not limited to, alix alba bark extract (willow bark), hamamelis Virginiana distillate (witch hazel), or a mixture thereof. Willow bark is a natural source of salicylic acid thought to clarify blemish-prone, oily or combination skin. Witch hazel is a natural astringent that gently leaves the complexion radiant. The advanced polymer technology soaks up excess oils and mattifies without leaving skin parched that aids in prevention of acne. The botanically derived agents help calm and sooth inflamed and irritated skin. The natural botanicals are an ideal antidote for hormonally out-of-control skin.

In certain other embodiments, the anti-inflammatory is an antihistamine. Suitable antihistamines for use in the present invention include, but are not limited to, brompheniramine maleate, diclofenac, carbenoxolone sodium, chlorpheniramine maleate, dexbrompheniramine, diphenhydramine hydrochloride, diphenylpyraline hydrochloride, doxylamine succinate, cetirizine HCL, cinnarazine, chlorphenhydramine maleate, naphazoline hydrochloride, pheniramine maleate, famotidine, flufenazine hydrochloride, ketotifen, omeprazole, pantoprazole sodium, ranitidine, cimetidine, cyproheptadine, clemastine, hyydroxyzine pamoate, doxephin HCL, loratadine, mebhydrolin naphthalenesulfonate, methapyrilene hydrochloride, orphenadrine citrate, pheniramine maleate, pyrilamine maleate, meclizine, quetiapine, ranitidine, terfenadine, thonzylamine hydrochloride, experimental H-3 and H-4 antagonists, for example, ABT-239, cipralisant, ciproxifan, clobenpropit, thioperamide, antazoline phosphate derivatives thereof, and mixtures thereof.

In certain embodiments, the skin care composition also includes an effective amount of an antioxidant which soothes the appearance of redness in skin. In certain embodiments, the antioxidant is present in an amount of from about 1.0 to 20.0 w/w % of the composition, more preferably from about 5.0 to 15.0 w/w %, and most preferably from about 10.0 to 15.0 w/w %. An antioxidant suitable for use in the present application includes, but is not limited, oleanolic acid, tea extracts, derivatives thereof, or mixtures thereof. Other suitable antioxidants for use in the present invention include, but are not limited to, 3-methyl-1-phenyl-2-pyrazolin-5-one, ebselen, pomiferin, trisodium ethylenediamine tetracetate, phytochemicals, nordihydroguaiaretic acid, green tea extracts, chromolaena odorata extracts, derivatives thereof, and mixtures thereof. In certain embodiments, the skin care composition may also include from about 0.001 to about 5.0 w/w % of an additive such as fragrance, pH adjuster, or the like.

In one embodiment, the topical skin care composition hereof includes about 5.0% benzoyl peroxide, from about 55% deionized water, 5.0% denatured alcohol or SD-40B alcohol or grain alcohol, 4.0% glycerine, 3.0% boswellia serrata extract, 3.0% ethoxydiglycol, 3.0% quercetin, 3.0% lecithin, 3.0% C12-C16 alcohols, 3.0% palmitic acid, 3.0% dimethicone, 3.0% cetyl alcohol, 2.0% stearyl alcohol, 2.0% glyceryl stearate, 2.0% PEG-100 stearate, 3.0% bentonite, 2.0% caprylic/capric triglyceride, 2.0% myristyl alcohol, 2.0% myristyl glucoside, 1.0% sorbitol, 1.0% glycyrrhiza glabra (licorice) root extract, 2.0% butylene glycol, 2.0% PEG-60 almond glycerides, 1.0% caprylyl glycol, 1.0% carbomer, 3.0% nordihydroguairaretic acid, 3.0% oleanic acid, 1.0% evodia rutecarpine fruit extract, 1.0% butylene glycol, 1.0% dipotassium glycyrrhizate, 1.0% camellia oleifera (Japanese green tea) extract, 1.0% camellia sinensis (white tea) leaf extract, 1.0% rosmarinus officinalis (rosemary) leaf extract, 1.0% caffeine, 1.0% superoxide dismutase, 1.0% disodium EDTA, 1.0% imidazolidinyl urea, 1.0% methylparaben, 1.0% propylparaben, 1.0% ethylparaben, 1.0% butylparaben, 1.0% titanium dioxide, 1.0% peppermint oil, 1.0% menthol, 1.0% fragrance, 1.0% citric acid and 1.0% TEA Carbomer.

In another embodiment, the topical skin care composition includes about 55.0% deionized water, 5.0% denatured alcohol SD-40B, 2.25% dimethicone, 3.5% glycerine, 3.0 boswellia serrata extract, 2.5% bentonite, 2.75 ethoxydiglycol and quercetin and ecithin and C12-C16 alcoahols-anpalrmitic acid, 2.0% stearyl alcohol, 2.25% cetyl alcohol, 1.75% glyceryl stearate and PEG-100 stearate, 1.5% capric/caprylic triglyceride, 1.25% myristyl alcohol and myristyl glucoside, 1.0 sorbitol, 1.0% glycyrrhiza glabra (Licorice) root extract, 1.0% butylene glycol and PEG-60 almond glycerides and caprylyl glycol and nordihydroguaiaretic acid and oleanic acid, 0.075% camellia oleifera (Japanese Green Tea) extract, camellia sinensis (White Tea) leaf extract, 1.0% evodia rutaecarpa fruit extract, 0.75% dipotassium glycyrrhitinate, 0.75% rosmarinus officinal (Rosemary) leaf extract, 0.75% caffeine, 0.75 superoxide dismutase, 0.75% disodium EDTA, 0.75% sorbitol, 0.75% tea carbomer, 0.5% imadazolidinyl urea and methylparaben and propylparaben and ethylparaben and butylparaben, 0.1% titanium dioxide, 0.015% peppermint essential oil, 0.01% menthol, and 0.01% citric acid.

In an alternate embodiment, the topical skin care composition includes deionized water, benzoyl peroxide, dimethicone, glycerine, bentonite, stearyl alcohol, cetyl alcohol, glyceryl stearate, PEG-100 stearate, capric caprylic triglyceride, myristyl alcohol, myristyl glucoside, glycyrrhiza glabra (licorice) root extract, oleanic acid, nordihydroguaiaretic acid, osmotic gel, dipotassium glycyrrhitinate, white tea extract, caffeine, superoxide dismutase, disodium EDTA, imidazolidinyl urea, methyl, paraben, probylparaben, ethlyparaben, and butylparaben.

In yet another embodiment, a topical skin care composition includes deionized water, ethoxydiglycol or butylene glycol, dimethicone, glycerine, bentonite, stearyl alcohol, cetyl alcohol, glyceryl stearate, PEG-100 stearate, salicylic acid, capric caprylic triglyceride, myristyl alcohol, myristyl glucoside, glycyrrhiza glabra (licorice) root extract, oleanic acid, nordihydroguaiaretic acid, osmotic gel, dipotassium glycyrrhitinate, white tea extract, caffeine, superoxide dismutase, disodium EDTA, imidazolidinyl urea, methyl, paraben, propylparaben, ethylparaben, and butylparaben.

From the foregoing it will be seen that this invention is one well adapted to attain all ends and objects hereinabove set forth together with the other advantages which are obvious and which are inherent to the composition. It will be understood that certain features and subcombinations may be employed without reference to other features and subcombinations. This is contemplated by and is within the scope of the claims. Since many possible embodiments may be made of the invention without departing from the scope thereof, it is to be understood that all matter herein set forth is to be interpreted as illustrative, and not in a limiting sense.

What is claimed is:
1. A topical skin care composition consisting essentially of:
about 5 w/w % benzoyl peroxide;
water;
Bentonite;
Boswellia Serrata Extract;
Butylene Glycol;
Butylparaben;
C 12-C 16 Alcohols;
Caffeine;
Camellia Oleifera (Japanese Green Tea) Leaf Extract;
Camellia Sinensis (Japanese White Tea) Leaf Extract;
Caprylic/Capric Triglyceride;
Carprylyl Glycol;
Cetyl Alcohol;
Citric Acid;
denatured Alcohol; Dimethicone;
Dipotassium Glycyrrhizate;
Disodium EDTA;
Ethoxydiglycol;
Ethylparaben;
Evodia Rutaecarpine Extract;
Glycerine;
Glyceryl Stearate;
Glycyrrhiza Glabra (Licorice) Root Extract;
Imidazolidinyl Urea;
Lecithin;
Menthol;
Methylparaben;
Myristyl Alcohol;
Myristyl Glucoside;
Nordihydroguaiaretic Acid;
Oleanolic Acid;
Palmitic Acid;
PEG-100 Stearate;
PEG-60 Almond Glycerides;
Peppermint Essential Oil;
Propylparaben;
Quercetin;
Rosmarinus Officinalis (Rosemary) Leaf Extract;
Sorbitol;
Stearyl Alcohol;
Superoxide Dismutase;
Tea Carbomer; and
Titanium Dioxide.

* * * * *